(12) United States Patent
Hokari et al.

(10) Patent No.: US 8,846,097 B2
(45) Date of Patent: Sep. 30, 2014

(54) PROCESS FOR PRODUCING ORGANIC-MODIFIED INORGANIC FINE PARTICLES

(75) Inventors: Hirofumi Hokari, Chino (JP); Sukenori Ichikawa, Suwa (JP)

(73) Assignee: Seiko Epson Corporation (JP)

( * ) Notice: Subject to any disclaimer, the term of this patent is extended or adjusted under 35 U.S.C. 154(b) by 340 days.

(21) Appl. No.: 13/227,784

(22) Filed: Sep. 8, 2011

(65) Prior Publication Data

US 2012/0065383 A1 Mar. 15, 2012

(30) Foreign Application Priority Data

Sep. 9, 2010 (JP) .................................. 2010-201664

(51) Int. Cl.
*A61K 9/14* (2006.01)
*A61K 9/16* (2006.01)
*B05D 3/02* (2006.01)

(52) U.S. Cl.
USPC ........................... 424/489; 424/490; 427/384

(58) Field of Classification Search
None
See application file for complete search history.

(56) References Cited

U.S. PATENT DOCUMENTS 5,204,031 A * 4/1993 Watanabe et al. ............. 264/656
6,986,943 B1 * 1/2006 Cook et al. .................... 428/402

2007/0003463 A1 1/2007 Ajiri
2010/0092663 A1 4/2010 Ajiri
2010/0104858 A1 * 4/2010 Horio et al. ................... 428/331

FOREIGN PATENT DOCUMENTS

| EP | 1 739 139 | 1/2007 |
| JP | 2006-282503 | 10/2006 |
| JP | 2010-055770 A | 3/2010 |
| JP | 2010-072688 A | 4/2010 |

OTHER PUBLICATIONS

Zhang, Jing et al., "Colloidal Ceria Nanocrystals: A Tailor-Made Crystal Morphology in Supercritical Water", Advanced Materials, vol. 19, $2^{nd}$ Issue, pp. 203-206, 2007.

* cited by examiner

*Primary Examiner* — Susan Tran
(74) *Attorney, Agent, or Firm* — Harness, Dickey & Pierce, P.L.C.

(57) ABSTRACT

A process is provided that includes performing a high-temperature high-pressure hydrothermal treatment for a reaction liquid prepared as a mixture of an acylated inorganic fine particle precursor and an organic modifying agent that has a carboxyl group. Because the reaction liquid contains the acylated inorganic fine particle precursor in advance, the grain growth during the high-temperature high-pressure hydrothermal treatment can be suppressed. The process thus enables production of organic-modified inorganic fine particles of a size about the same as or even smaller than that before the high-temperature high-pressure hydrothermal treatment.

2 Claims, 2 Drawing Sheets

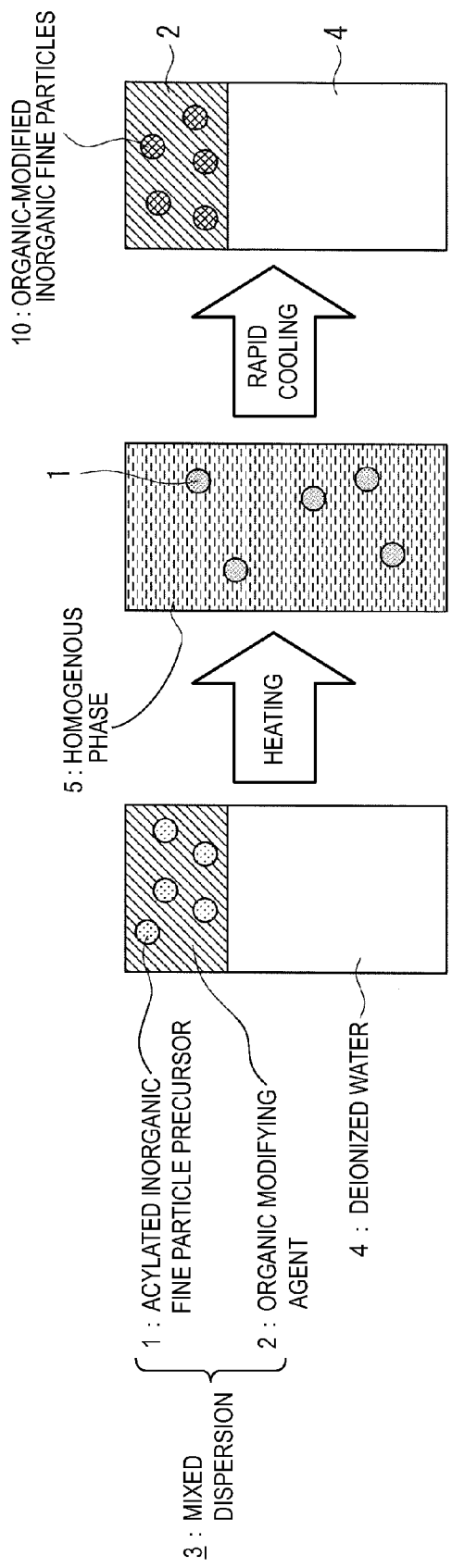

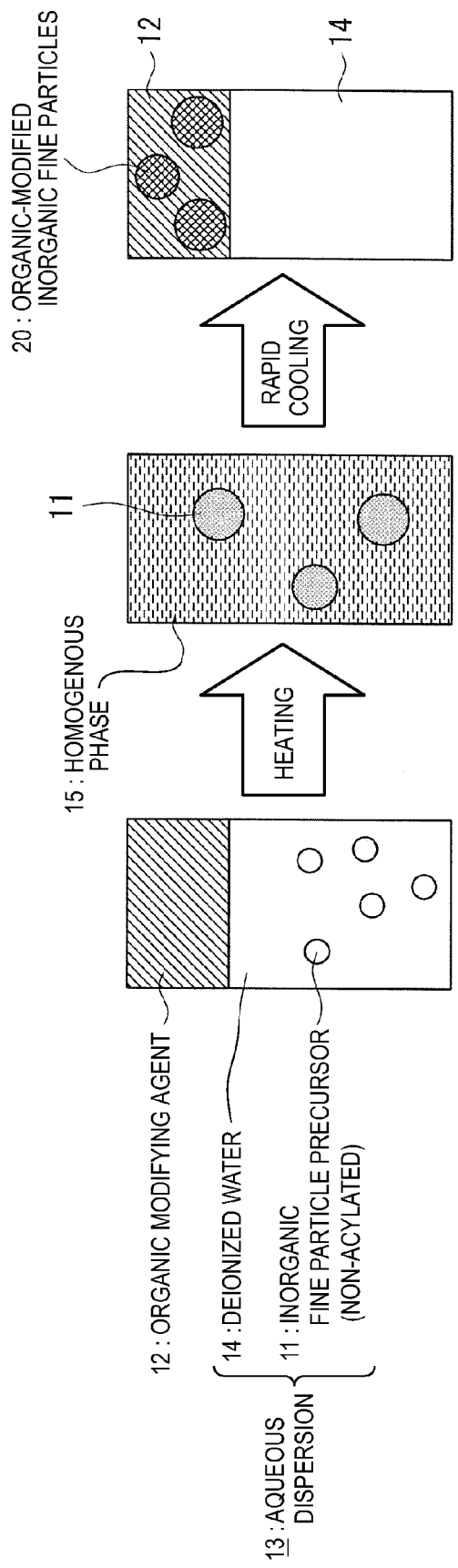

PROCESS FOR PRODUCING ORGANIC-MODIFIED INORGANIC FINE PARTICLES

The entire disclosure of Japanese Patent Application No. 2010-201664, filed Sep. 9, 2010 is expressly incorporated by reference herein.

BACKGROUND

1. Technical Field

The present invention relates to organic-modified inorganic fine particle producing processes.

2. Related Art

Fine particles of a particle diameter no greater than several micrometers, particularly nanometer-sized particles (nanoparticles) have generated interest as material that exhibits desirable functions, such as in industrial materials (ceramic nanostructure modifying agents, optical functional coating materials, electromagnetic wave shielding materials, secondary battery materials, fluorescence materials, electronic component materials, magnetic recording materials, and polishing materials), and drug and cosmetic materials, and have potential in a wide range of applications, as described in, for example, JP-A-2006-282503.

Practical application of nanoparticles requires adding specific functions to different fine particles. To this end, a technique that can be used to modify the particle surface needs to be established. One such method of adding functions is organic modification, which can be stably used for fine particles, particularly for nanoparticles.

For example, the foregoing patent publication and J. Zhang, et al., ADVANCED MATERIALS, 2007, Vol. 19, No. 2, p. 203-206 describe modifying the surface of inorganic fine particles with an organic group through a supercritical hydrothermal synthesis reaction performed after an aqueous dispersion of an inorganic fine particle precursor in water is introduced into a reaction tube with an organic modifying agent.

Upon testing the methods described in these and other publications by experiments conducted by the present inventors, it was found that the particle diameter has the tendency to coarsely increase in the process of organic modification, and that adjusting only the amount of organic modifying agent added may fail to sufficiently control the particle diameter.

SUMMARY

An advantage of some aspects of the invention is to provide an organic-modified inorganic fine particle producing process with which the grain growth during high-temperature high-pressure hydrothermal treatment can be suppressed.

An aspect of the invention is directed to an organic-modified inorganic fine particle producing process that includes performing a high-temperature high-pressure hydrothermal treatment for a reaction liquid prepared as a mixture of an acylated inorganic fine particle precursor and an organic modifying agent that has a carboxyl group and is used for the acylation of an inorganic fine particle precursor. In this way, because the acylated inorganic fine particle precursor is already present prior to the reaction, the grain growth during the high-temperature high-pressure hydrothermal treatment can be suppressed. The process thus enables production of organic-modified inorganic fine particles of a size about the same as or even smaller than that before the high-temperature high-pressure hydrothermal treatment. Note that the "mixture" corresponds to mixed dispersion 3, as will be described later.

The organic-modified inorganic fine particle producing process may further include allowing the inorganic fine particle precursor to react with the organic modifying agent to acylate the inorganic fine particle precursor prior to the high-temperature high-pressure hydrothermal treatment. In this way, the mixture (reaction liquid) containing the inorganic fine particle precursor and the organic modifying agent is naturally prepared in the process of acylating the inorganic fine particle precursor. Thus, the labor required to prepare the mixture can be eliminated or reduced.

The organic-modified inorganic fine particle producing process may further include mixing water with a metal compound that produces the inorganic fine particle precursor by hydrolysis reaction, so as to prepare a raw material sol prior to the acylation of the inorganic fine particle precursor, the organic modifying agent being added to the raw material sol in the acylation of the inorganic fine particle precursor. In this way, the isopropoxy group can be substituted with the hydroxyl group even when, for example, titanium tetraisopropoxide ($Ti(O^iPr)_4$) is used as the metal compound that produces the inorganic fine particle precursor by hydrolysis reaction. The hydroxyl group can then easily be substituted with an acyl group with the organic modifying agent. Acylation of $Ti(O^iPr)_4$ can thus be easily performed, and the coarse increase in particle diameter during the high-temperature high-pressure hydrothermal treatment can be suppressed.

The invention is applicable to areas related to surface-modified inorganic fine particle materials, for example, such as lens coating materials, electronic component materials, and secondary battery materials.

BRIEF DESCRIPTION OF THE DRAWINGS

The invention will be described with reference to the accompanying drawings, wherein like numbers reference like elements.

FIG. 1 shows diagrams representing a producing process of organic-modified inorganic fine particles according to an embodiment of the invention.

FIG. 2 shows diagrams representing a producing process of organic-modified inorganic fine particles according to a comparative configuration.

DESCRIPTION OF EXEMPLARY EMBODIMENTS

An embodiment of the invention is described below with reference to the accompanying drawings. In the appended figures, members with the same configurations are given the same reference numerals, and will be described only once.

1. Embodiment

FIG. 1 shows schematic diagrams representing the process for producing organic-modified inorganic fine particles 10 according to an embodiment of the invention.

First, in (a) in FIG. 1, the raw material inorganic fine particle precursor 1 and an organic modifying agent 2 are mixed to acylate the inorganic fine particle precursor 1. The inorganic fine particle precursor 1 is, for example, inorganic metal oxide or inorganic metal hydroxide, and has a particle diameter of no greater than several micrometers. The organic modifying agent 2 is a modifying agent with a carboxyl group, for example, a carboxylic acid with a long-chain alkyl group. The mixture of the acylated inorganic fine particle precursor 1 and the organic modifying agent 2, specifically a mixed dispersion 3 of the acylated inorganic fine particle precursor 1 in the organic modifying agent 2, is then used as a reaction liquid, and is charged into a reaction chamber with deionized water 4.

The reaction chamber is sealed, and heated to subject the mixed dispersion 3 to a high-temperature high-pressure hydrothermal treatment. As illustrated in (b) in FIG. 1, in the high-temperature high-pressure hydrothermal treatment, the deionized water 4 in the reaction chamber becomes supercritical or subcritical, and mixes with the mixed dispersion 3 to form a homogeneous phase 5. Specifically, the aqueous phase and the organic phase are homogeneously mixed. The homogeneous phase 5 as a homogeneous mixture of the aqueous phase and the organic phase serves as a reaction field to organically modify the surface of the inorganic fine particle precursor 1. Here, the inorganic fine particle precursor 1 undergoes only limited grain growth (specifically, formation of coarse particle diameters is suppressed).

Thereafter, the reaction chamber is rapidly cooled to stop the organic modification reaction in the reaction chamber. As illustrated in (c) in FIG. 1, the aqueous phase and the organic phase separate with the temperature decrease. Organic-modified inorganic fine particles 10 are then collected from the reaction chamber.

Because the acylated inorganic fine particle precursor 1 is contained as a reaction precursor in this producing process, the grain growth during the high-temperature high-pressure hydrothermal treatment can be suppressed. The organic-modified inorganic fine particles 10 can thus have about the same or even smaller particle diameters than those before the high-temperature high-pressure hydrothermal treatment. Specifically, the particle diameter of the reaction product organic-modified inorganic fine particles 10 can be controlled by controlling the particle diameter of the reaction precursor.

The following describes Examples 1 and 2. In Examples 1 and 2, the particle diameter of the organic-modified inorganic fine particles 10 obtained by the producing process of the embodiment above was confirmed by the experiment actually conducted by the present inventors. The results of the experiment are also presented.

1-1. Example 1

In Example 1, amorphous titanium dioxide (a-$TiO_2$) was selected as the inorganic fine particle precursor (metal oxide) 1, and oleic acid ($C_{17}H_{33}COOH$) as the organic modifying agent 2.

First, 0.003 g of amorphous titanium dioxide (Wako Pure Chemical Industries, Ltd.) was acylated with 0.5 mL of oleic acid (Kanto Kagaku) using an ultrasonic process to prepare a mixed dispersion as a dispersion of the acylated amorphous titanium dioxide. The mixed dispersion represents the reaction liquid of Example 1.

In order to confirm the particle diameter of the acylated amorphous titanium dioxide before high-temperature high-pressure hydrothermal treatment, the particles contained in the mixed dispersion were centrifuged, and dispersed again in hexane ($C_6H_{14}$) to measure the particle size distribution using a microtrack ultrafine particle size analyzer (UPA-EX250; Nikkiso Co., Ltd.) (see *A1).

0.5 mL of the mixed dispersion was then charged into a tubular, pressure-resistant reaction chamber (5-cc volume; hereinafter, also referred to simply as reaction chamber) with 2.0 mL of deionized water. High-temperature high-pressure hydrothermal treatment was performed by placing the reaction chamber in a 400° C. furnace, and by raising the temperature inside the reaction chamber from room temperature to 400° C. in 2 min (about 3° C./sec), and maintaining the temperature at 400° C. for 10 min.

The reaction chamber was taken out of the furnace, and rapidly cooled by being immersed in a water bath to stop the organic modification reaction in the reaction chamber. The reaction product was then collected from the reaction chamber, and centrifuged to obtain organically modified titania particles. Powder X-ray diffractometry revealed that the crystalline structure of the organically modified titania particles was of the anatase-type titanium oxide.

In order to confirm the particle diameter of the organically modified anatase-type titanium oxide after the high-temperature high-pressure hydrothermal treatment, the particles were dispersed again in hexane, and the particle size distribution was measured using the microtrack ultrafine particle size analyzer (UPA-EX250) (see *A2).

The results of the particle size distribution measurements before and after the high-temperature high-pressure hydrothermal treatment are as follows.

*A1: The particle diameter of the amorphous titanium dioxide in the hexane dispersion before the high-temperature high-pressure hydrothermal treatment was 0.1 μm.

*A2: The particle diameter of the organically modified anatase-type titanium oxide in the hexane dispersion after the high-temperature high-pressure hydrothermal treatment was 0.15 μm.

From these results and the results of Comparative Example 1 (described later; see *C1, C2), it was found that the grain growth during the high-temperature high-pressure hydrothermal treatment could be suppressed to limit the particle diameter of the organically modified anatase-type titanium oxide.

1-2. Example 2

In Example 2, lanthanum hydroxide ($La(OH)_3$) was selected as the inorganic fine particle precursor (metal hydroxide) 1, and oleic acid as the organic modifying agent 2.

First, 0.008 g of lanthanum hydroxide(III) (Kojundo Chemical Laboratory Co., Ltd.) was acylated with 0.5 mL of oleic acid (Kanto Kagaku) using an ultrasonic process to prepare a mixed dispersion as a dispersion of acylated lanthanum hydroxide. The mixed dispersion represents the reaction liquid of the Example 2.

In order to confirm the particle diameter of the acylated lanthanum hydroxide before high-temperature high-pressure hydrothermal treatment, the particles contained in the mixed dispersion were centrifuged, and dispersed again in hexane to measure the particle size distribution using the microtrack ultrafine particle size analyzer (UPA-EX250) as in Example 1 (see *B1).

0.5 mL of the mixed dispersion was then charged into a tubular, pressure-resistant reaction chamber (5-cc volume) with 2.0 mL of deionized water. Heating and cooling in the next high-temperature high-pressure hydrothermal treatment were performed in the same manner as in Example 1. After cooling, the reaction product was collected from the reaction chamber, and centrifuged to obtain organically modified lanthanum hydroxide.

In order to confirm the particle diameter of the organically modified lanthanum hydroxide after the high-temperature high-pressure hydrothermal treatment, the particles were dispersed again in hexane, and the particle size distribution was measured using the microtrack ultrafine particle size analyzer (UPA-EX250) (see *B2).

The results of the particle size distribution measurements before and after the high-temperature high-pressure hydrothermal treatment are as follows.

*B1: The particle diameter of the lanthanum hydroxide in the hexane dispersion before the high-temperature high-pressure hydrothermal treatment was 2 μm.

*B2: The particle diameter of the organically modified lanthanum hydroxide in the hexane dispersion after the high-temperature high-pressure hydrothermal treatment was 0.003 μm.

From these results and the results of Comparative Example 2 (see *D1, D2), it was confirmed that the grain growth during the high-temperature high-pressure hydrothermal treatment could be suppressed to limit the particle diameter of the organically modified lanthanum hydroxide.

2. Other Embodiments

2-1. Separate Acylation

The foregoing embodiment described obtaining the acylated inorganic fine particle precursor 1 through the reaction of the inorganic fine particle precursor 1 with the organic modifying agent 2. In this way, the mixed dispersion (reaction liquid) containing the inorganic fine particle precursor and the organic modifying agent naturally forms in the process of acylating the inorganic fine particle precursor, and thus the labor required to prepare the mixed dispersion can be eliminated or reduced.

The invention, however, is not limited to this. In the invention, the acylated inorganic fine particle precursor may be separately obtained in a different step by the reaction of the inorganic fine particle precursor and the acylating agent. The inorganic fine particle precursor 1 so obtained may then be mixed with the organic modifying agent 2 and dispersed therein to prepare the mixed dispersion 3. The mixed dispersion 3 can then be used as a reaction liquid to perform the high-temperature high-pressure hydrothermal treatment. The organic-modified inorganic fine particles with the limited grain growth also can be produced as in the foregoing embodiment in this manner.

2-2. Solation as Pretreatment

In the invention, the inorganic fine particle precursor may be formed into a sol to make the acylation easier, prior to being acylated. Specifically, an acylation pretreatment may be performed in which deionized water is added to the metal compound that produces the inorganic fine particle precursor through hydrolysis reaction, and the mixture is subjected to, for example, an ultrasonic process to form a raw material sol that contains the inorganic fine particle precursor. The organic modifying agent may then be added to the raw material sol to make the reaction liquid.

In this way, for example, even with the use of titanium tetraisopropoxide ($Ti(O^iPr)_4$) as the metal compound, the isopropoxy group can be substituted with the hydroxyl group by hydrolysis. The hydroxyl group can then be easily substituted with an acyl group with the organic modifying agent. Acylation of $Ti(O^iPr)_4$ can thus be performed easily, and the grain growth during the high-temperature high-pressure hydrothermal treatment can be suppressed.

2-3. Other Examples of Inorganic Fine Particle Precursor

The foregoing described selecting amorphous titanium dioxide as the inorganic fine particle precursor (metal oxide), and lanthanum hydroxide as the inorganic fine particle precursor (metal hydroxide). However, in the invention, the type of inorganic fine particle precursor is not limited to these.

For example, the metal oxide may be selected from, for example, zirconia (zirconium dioxide: $ZrO_2$), cerium oxide ($CeO_2$), iron oxide ($Fe_2O_3$, $Fe_3O_4$), titanium oxide ($TiO_2$), and zinc oxide ($ZnO$). The metal hydroxide may be selected from, for example, zirconium hydroxide ($Zr(OH)_4$), cerium hydroxide ($Ce(OH)_4$), cobalt hydroxide ($Co(OH)_2$), and gadolinium hydroxide ($Gd(OH)_2$). The grain growth during the high-temperature high-pressure hydrothermal treatment also can be suppressed by acylating these inorganic fine particle precursors in advance.

2-4. Other Examples of Metal Compound

Similarly, the type of the metal compound that produces the inorganic fine particle precursor by hydrolysis reaction is not limited to titanium tetraisopropoxide ($Ti(O^iPr)_4$). In the invention, the metal compound may be selected from a variety of metal organic compounds and metal inorganic salts. Examples of metal organic compounds include metal alkoxide, acetylacetonate, and acetate. Examples of metal inorganic salts include nitrates such as cerium nitrate ($Ce(NO_3)_3$), iron nitrate ($Fe(NO_3)_3$), and zinc nitrate ($Zn(NO_3)_2$). The raw material sol can be prepared by adding water (necessary for hydrolysis), and an acid or a base (pH adjuster, reaction catalyst) to the metal compound, followed by, for example, an ultrasonic process.

For example, when a nitrate is selected as the metal compound, a metal hydroxide can be formed by hydrolysis reaction. The hydroxyl group of the metal hydroxide can easily be substituted with an acyl group with the organic modifying agent. Acylation of the nitrate can thus be performed easily, and the grain growth during the high-temperature high-pressure hydrothermal treatment can be suppressed.

3. Comparative Configuration of the Invention

A comparative configuration is described below.

FIG. 2 shows schematic diagrams representing the process for producing organic-modified inorganic fine particles according to the comparative configuration.

First, in (a) in FIG. 2, the raw material inorganic fine particle precursor 11 and deionized water 14 are mixed to prepare an aqueous dispersion 13 of the inorganic fine particle precursor 11 dispersed in the deionized water 14. The aqueous dispersion 13 is then charged into a reaction chamber with an organic modifying agent 12.

The reaction chamber is sealed, and heated to subject the aqueous dispersion 13 and the organic modifying agent 12 to a high-temperature high-pressure hydrothermal treatment. Then, as illustrated in (b) in FIG. 2, in the high-temperature high-pressure hydrothermal treatment, the deionized water 14 in the reaction chamber becomes supercritical, and mixes with the organic modifying agent 12 to form a homogeneous phase 15. Specifically, the aqueous phase and the organic phase are mixed homogenously. The homogeneous phase 15 as a homogenous mixture of the aqueous phase and the organic phase serves as a reaction field to organically modify the surface of the inorganic fine particle precursor 11. The reaction chamber is then rapidly cooled to stop the organic modification reaction in the reaction chamber. As illustrated in (c) in FIG. 2, the aqueous phase and the organic phase separate with the temperature decrease. Organic-modified inorganic fine particles 20 are then collected from the reaction chamber.

Comparative Examples 1 and 2 are described below.

In Comparative Examples 1 and 2, the particle diameter of the organic-modified inorganic fine particles 20 obtained by the producing process according to the foregoing comparative configuration was confirmed by the experiment actually conducted by the present inventors. The results of the experiment are also presented.

3-1. Comparative Example 1

In Comparative Example 1, amorphous titanium dioxide was selected as the inorganic fine particle precursor (metal oxide) 11, and oleic acid as the organic modifying agent 12, as in Example 1. Instead of the mixed dispersion described in Example 1, an aqueous dispersion was prepared by dispersing 0.003 g of amorphous titanium dioxide in 2.0 mL of deionized water. Specifically, in Comparative Example 1, the amorphous titanium dioxide was dispersed in deionized water to prepare an aqueous dispersion, without being acylated in advance.

In order to confirm the particle diameter of the amorphous titanium dioxide before high-temperature high-pressure hydrothermal treatment, the particle size distribution of the particles contained in the aqueous dispersion was measured using a microtrack ultrafine particle size analyzer (UPA-EX250) as in Example 1 (see *C1).

Thereafter, 2.0 mL of the aqueous dispersion was charged into a tubular, pressure-resistant reaction chamber (5-cc volume) with oleic acid. Two samples with different oleic acid amounts, 0.1 mL and 0.5 mL, were prepared. Heating and cooling in the next high-temperature high-pressure hydrothermal treatment were performed in the same manner as in Example 1. After cooling, the reaction product was collected from the reaction chamber, and centrifuged to obtain organically modified titanium dioxide. Powder X-ray diffractometry revealed that the crystalline structure of the organically modified titanium dioxide was of the anatase-type titanium oxide.

In order to confirm the particle diameter of the organically modified anatase-type titanium oxide after the high-temperature high-pressure hydrothermal treatment, the particles were dispersed again in hexane, and the particle size distribution was measured using the microtrack ultrafine particle size analyzer (UPA-EX250) (see *C2).

The results of the particle size distribution measurements before and after the high-temperature high-pressure hydrothermal treatment are as follows.

*C1: The particle diameter of the amorphous titanium dioxide in the aqueous dispersion before the high-temperature high-pressure hydrothermal treatment was 0.1 µm.

*C2: The particle diameter of the organically modified anatase-type titanium oxide in the hexane dispersion after the high-temperature high-pressure hydrothermal treatment was 1 µm (with addition of 0.1 mL oleic acid), and 1.5 µm (with addition of 0.5 mL oleic acid).

In Comparative Example 1, the particle diameter increase after the high-temperature high-pressure hydrothermal treatment was 10 fold or higher. It was also confirmed that the particle diameter of the organically modified anatase-type titanium oxide could be controlled by adjusting the amount of oleic acid added. It was, however, not possible to suppress the particle diameter at the level of Example 1.

3-2 Comparative Example 2

In Comparative Example 2, lanthanum hydroxide was selected as the inorganic fine particle precursor (metal hydroxide) 11, and oleic acid as the organic modifying agent 12, as in Example 2. Instead of the mixed dispersion described in Example 2, 0.008 g of lanthanum hydroxide was dispersed in 2.0 mL of deionized water to prepare an aqueous dispersion. Specifically, in Comparative Example 2, the lanthanum hydroxide was dispersed in deionized water to prepare an aqueous dispersion, without being acylated in advance.

In order to confirm the particle diameter of the lanthanum hydroxide before high-temperature high-pressure hydrothermal treatment, the particle size distribution of the particles contained in the aqueous dispersion was measured using the microtrack ultrafine particle size analyzer (UPA-EX250) as in Example 2 (see :D1).

Thereafter, 2.0 mL of the aqueous dispersion was charged into a tubular, pressure-resistant reaction chamber (5-cc volume) with the oleic acid. Two samples with different oleic acid amounts, 0.1 mL and 0.5 mL, were prepared. Heating and cooling in the next high-temperature high-pressure hydrothermal treatment were performed in the same manner as in Example 2. After cooling, the reaction product was collected from the reaction chamber, and centrifuged to obtain organically modified lanthanum hydroxide.

In order to confirm the particle diameter of the organically modified lanthanum hydroxide after the high-temperature high-pressure hydrothermal treatment, the particles were dispersed again in hexane, and the particle size distribution was measured using the microtrack ultrafine particle size analyzer (UPA-EX250) (see *D2).

The results of the particle size distribution measurements before and after the high-temperature high-pressure hydrothermal treatment are as follows.

*D1: The particle diameter of the lanthanum hydroxide in the aqueous dispersion before the high-temperature high-pressure hydrothermal treatment was 2 µm.

*D2: The particle size of the organically modified lanthanum hydroxide in the hexane dispersion after the high-temperature high-pressure hydrothermal treatment was 1.5 µm (with addition of 0.1 mL oleic acid), and 0.02 µm (with addition of 0.5 mL oleic acid).

In Comparative Example 2, the particle diameter became smaller in the both samples after the high-temperature high-pressure hydrothermal treatment. It was also confirmed that the particle diameter could be controlled by adjusting the amount of oleic acid added. It was, however, not possible to suppress the particle diameter at the level of Example 2.

What is claimed is:

1. A process for producing organic-modified inorganic fine particles, comprising:
    acylating inorganic fine particles by mixing the inorganic fine particles with an organic modifying agent that has a carboxyl group to form a mixture of acylated fine particles and the organic modifying agent;
    charging the mixture of the acylated fine particles and the organic modifying agent into a vessel including deionized water;
    performing a hydrothermal treatment on the mixture and the deionized water to form a homogeneous mixture of acylated fine particles, the organic modifying agent, and deionized water; and
    cooling the homogenous mixture,
    wherein the hydrothermal treatment raises the temperature of the mixture and the deionized water to about 400° C. in two minutes, and maintaining the temperature at 400° C. for 10 minutes.

2. The process according to claim 1, wherein the step of preparing the acylated inorganic fine particles includes reacting the inorganic fine particles with the organic modifying agent.

* * * * *